(12) United States Patent
Kusters (10) Patent No.: US 10,918,780 B2
(45) Date of Patent: Feb. 16, 2021

(54) SYSTEM AND METHOD OF CONTROLLING MEMBRANE FLUID FLOW USING FLUID OUTPUT

(71) Applicant: Fenwal, Inc., Lake Zurich, IL (US)

(72) Inventor: Benjamin E. Kusters, Pleasant Prairie, WI (US)

(73) Assignee: Fenwal, Inc., Lake Zurich, IL (US)

(*) Notice: Subject to any disclaimer, the term of this patent is extended or adjusted under 35 U.S.C. 154(b) by 235 days.

(21) Appl. No.: 16/108,471

(22) Filed: Aug. 22, 2018

(65) Prior Publication Data

US 2019/0060547 A1 Feb. 28, 2019

Related U.S. Application Data

(60) Provisional application No. 62/548,603, filed on Aug. 22, 2017.

(51) Int. Cl.
*A61M 1/34* (2006.01)
*A61M 1/02* (2006.01)
*A61M 1/26* (2006.01)
*B01D 63/16* (2006.01)

(52) U.S. Cl.
CPC ............ *A61M 1/3496* (2013.01); *A61M 1/02* (2013.01); *A61M 1/262* (2014.02); *A61M 1/3406* (2014.02); *B01D 63/16* (2013.01)

(58) Field of Classification Search
CPC ........................... B01D 2313/13; B01D 65/08; B01D 2321/20; B01D 24/48; B01D 37/04; B01D 37/046; B01D 61/22; A61M 2202/0429; A61M 1/16; A61M 1/3403; A61M 2205/3334; A61M 2202/0415; A61M 1/1601
See application file for complete search history.

(56) References Cited

U.S. PATENT DOCUMENTS 5,053,121 A  10/1991  Schoendorfer et al.
5,194,145 A   3/1993  Schoendorfer
(Continued)

FOREIGN PATENT DOCUMENTS

WO    WO 92/02264 A1    2/1992

OTHER PUBLICATIONS

Extended European Search Report, counterpart EP Appl. No. EP18188867, dated Jan. 18, 2019 (8 pages).

*Primary Examiner* — Ana M Fortuna
(74) *Attorney, Agent, or Firm* — Cook Alex Ltd.

(57) ABSTRACT

A computer-implemented method for controlling fluid flow rates during a biological fluid procedure, comprising providing a membrane separator configured to separate a biological fluid into filtrate and retentate, wherein concentration of retentate exiting the membrane separator is controllable by altering a flow rate of the retentate exiting the membrane separator. The computer-implemented method also comprises detecting a change of attenuated retentate particles within the filtrate, comparing the change of attenuated retentate particles within the filtrate with a threshold level, and providing a response action comprising altering the concentration of retentate exiting the membrane separator if the change of attenuated retentate particles within the filtrate exceeds the threshold level.

17 Claims, 5 Drawing Sheets

(56) References Cited

U.S. PATENT DOCUMENTS

| | | | | |
|---|---|---|---|---|
| 5,702,597 | A * | 12/1997 | Chevallet | A61M 1/1656 |
| | | | | 210/195.2 |
| 5,958,244 | A * | 9/1999 | Hartmann | B01D 61/025 |
| | | | | 210/195.2 |
| 6,296,770 | B1 * | 10/2001 | Wilcox | B01D 61/147 |
| | | | | 210/195.2 |
| 6,419,822 | B2 | 7/2002 | Muller et al. | |
| 7,789,245 | B2 * | 9/2010 | Westberg | B04B 5/0442 |
| | | | | 210/360.1 |
| 8,691,086 | B2 * | 4/2014 | Oklejas, Jr. | B01D 65/027 |
| | | | | 210/134 |
| 8,840,790 | B2 | 9/2014 | Wegener et al. | |
| 10,046,278 | B2 * | 8/2018 | Kusters | C12N 5/0644 |
| 10,130,751 | B2 * | 11/2018 | Radwanski | A61M 1/3692 |
| 10,682,611 | B2 * | 6/2020 | Brown | B01D 61/22 |
| 2002/0033367 | A1 * | 3/2002 | Prince | A61M 1/265 |
| | | | | 210/650 |
| 2011/0315632 | A1 * | 12/2011 | Freije, III | B01D 65/02 |
| | | | | 210/636 |
| 2012/0273416 | A1 | 11/2012 | Wegener et al. | |
| 2014/0074007 | A1 * | 3/2014 | McNeil | B01J 20/3212 |
| | | | | 604/4.01 |
| 2016/0378298 | A1 | 12/2016 | Planas et al. | |

* cited by examiner

SYSTEM AND METHOD OF CONTROLLING MEMBRANE FLUID FLOW USING FLUID OUTPUT

CROSS-REFERENCE TO RELATED APPLICATIONS

This application claims the benefit of U.S. Provisional Patent App. No. 62/548,603 filed Aug. 22, 2017, which is expressly incorporated herein by reference in its entirety.

FIELD OF THE DISCLOSURE

The present disclosure relates generally to systems and methods for membrane separation of biological fluid and, in particular to systems and methods for controlling membrane fluid flow using fluid output parameters.

BACKGROUND

A variety of available blood processing systems allows for the collection and processing of particular blood components, rather than whole blood, from donors or patients. In the case of a blood donor, whole blood is drawn from the donor, a desired blood constituent isolated and collected, and the remaining blood components returned to the donor. By removing only particular constituents rather than whole blood, it takes the donor's body a shorter time period to recover to normal blood levels, thereby increasing the frequency with which the donor may donate blood. It is beneficial to increase in this manner the overall supply of blood constituents made available for health care, such as red blood cells (RBCs), leukocytes, plasma, and/or platelets, etc.

The separation phase of blood components from whole blood may be achieved through a spinning membrane or centrifugation, in which whole blood is passed through a centrifuge or membrane after it is withdrawn from the patient. To avoid contamination and possible infection of the patient, the blood is preferably contained within a sealed, sterile fluid flow system during the entire separation process. Typical blood processing systems thus may include a permanent, reusable hardware assembly containing the hardware (drive system, pumps, valve actuators, programmable controller, and the like) that pumps the blood, and a disposable, sealed and sterile fluid circuit that is mounted in cooperation on the hardware. In the case of separation via centrifugation, the hardware assembly includes a centrifuge that may engage and spin a separation chamber of the disposable fluid circuit during a blood separation step. The blood, however, may make actual contact only with the fluid circuit, which assembly may be used only once and then discarded. In the case of separation via a spinning membrane, a disposable single-use spinning membrane may be used in cooperation with the hardware assembly and disposable fluid circuit.

In the case of separation via centrifugation, as the whole blood is spun by the centrifuge, the heavier (greater specific gravity) components, such as red blood cells, move radially outwardly away from the center of rotation toward the outer or "high-G" wall of the separation chamber of the fluid circuit. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber of the fluid circuit.

In the case of separation via a spinning membrane, whole blood may be spun within a disposable spinning membrane, rather than within a separation chamber of a fluid circuit. Larger molecules, such as red blood cells, may be retained within one side of the membrane, while the smaller molecules, such as plasma, may escape through the pores of the membrane to the other side of the membrane. Various ones of these components can be selectively removed from the whole blood by forming appropriately located outlet ports in the housing of the membrane column. Various types of columns with different pore sizes may be used, depending on the components to be separated.

SUMMARY

According to an exemplary embodiment, the present disclosure is directed to a computer-implemented method for controlling fluid flow rates during a biological fluid procedure, comprising providing a membrane separator configured to separate a biological fluid into filtrate and retentate, wherein concentration of retentate exiting the membrane separator is controllable by altering a flow rate of the retentate exiting the membrane separator. The computer-implemented method also comprises detecting a change of attenuated retentate particles within the filtrate, comparing the change of attenuated retentate particles within the filtrate with a threshold level, and providing a response action comprising altering the concentration of retentate exiting the membrane separator if the change of attenuated retentate particles within the filtrate exceeds the threshold level.

According to an exemplary embodiment, the present disclosure is directed to a system for automated control and processing of a biological fluid flow, the system comprising a reusable separation apparatus controlled by a microprocessing controller unit. The system also comprises a disposable sterile circuit configured to associate with the reusable separation apparatus, the disposable sterile circuit comprising a membrane separator comprising a porous membrane, wherein the separator comprises an inlet, a first outlet for retentate, and a second outlet for filtrate. The reusable apparatus and microprocessing controller unit are configurable with an output concentration of retentate and configured to detect at the second outlet a change of attenuated retentate particles within the filtrate, compare the change of attenuated retentate particles with a threshold level, and provide a response action comprising altering the output concentration of retentate exiting the first outlet if the change of attenuated retentate particles exceeds the threshold level.

According to an exemplary embodiment, the present disclosure is directed to a computer-implemented method for controlling fluid flow rates during a blood processing procedure, comprising providing a spinning membrane separator configured to separate blood into plasma and cellular components, wherein hematocrit of the cellular components exiting the spinning membrane separator is controllable by altering a flow rate of the cellular components exiting the membrane separator. The computer-implemented method also comprises detecting a change of free hemoglobin within the plasma with an optical sensor, detecting a change in transmembrane pressure within the spinning membrane separator with a pressure sensor, comparing the change of free hemoglobin within the plasma with a first threshold level, comparing the change in transmembrane pressure with a second threshold level, altering the flow rate of the cellular components exiting the spinning membrane separator if the change of free hemoglobin exceeds the first threshold level, and altering the flow rate of the cellular components exiting the spinning membrane separator if the change of transmembrane pressure exceeds the second threshold level. The flow rate is not altered based on the change of free hemoglobin if the flow rate is already being altered based on the change of transmembrane pressure, and the flow rate is not altered based on the change of transmembrane pressure if the flow rate is already being altered based on the change of free hemoglobin.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may allow separation control process optimizations to be made in advance of red blood cell hemolysis induced by aggressive separation.

Some embodiments may minimize separation that generates hemolysis without significant membrane fouling by using free hemoglobin in the plasma line as the indicator for separation adjustments.

Some embodiments may provide a back-up system to minimize hemolysis during biological fluid processing by utilizing more than one indicator to detect and adjust for overaggressive separation.

The systems and methods of the present application may be advantageously implemented in various procedures in which a suspension of biological cells is separated into its constituents, such as in the separation or concentration of any of red blood cells, white blood cells, platelets, and/or plasma from whole blood or a blood product. A detailed description of a spinning membrane separator may be found in U.S. Pat. No. 5,194,145 to Schoendorfer, which is incorporated by reference herein in its entirety. This patent describes a membrane-covered spinner having an interior collection system disposed within a stationary shell. Blood may be fed into an annular space or gap between the spinner and the shell. The blood may move along the longitudinal axis of the shell toward an exit region, with plasma passing through the membrane and out of the shell into a collection bag. The remaining blood components, primarily red blood cells, platelets and white cells, may move to the exit region between the spinner and the shell and may be returned to the donor.

Spinning membrane separators have been found to provide improved filtration rates, due primarily to the unique flow patterns ("Taylor vortices") induced in the gap between the spinning membrane and the shell. The Taylor vortices may create shear forces in the gap that may help to keep the cells, proteins, and/or various biomolecules present in a biological fluid from depositing on and fouling or clogging the membrane.

When a membrane becomes fouled, the effective surface area of the membrane available for filtration may be decreased. As membrane surface area decreases, the separation efficiency of the device may be reduced, and a higher transmembrane pressure (TMP) may be required for filtration. It may often be desired to prevent, or at least limit, fouling of a membrane. Some degree of fouling may be acceptable, as it may be representative of an aggressive filtration procedure. However, excessive fouling may be indicative of overaggressive filtration that may lead to pressure and efficiency related issues.

In order to control fouling, the controllers for the separation systems may be programmed with control processes or algorithms that monitor the fouling rate, which is measured as a change in the TMP over time. Monitoring the fouling rate (mmHg/min) may provide the system with information required to control the filtration procedure parameters in an effort to reduce fouling in order to maintain fouling rates within predetermined limits. U.S. Pat. No. 8,840,790 and U.S. Provisional Pat. Appl. No. 62/334,249, which are incorporated by reference herein in their entireties, provide examples of methods for controlling fouling in a membrane separation system.

An aggressive filtration procedure may promote separation and procedure efficiency and performance. However, an overaggressive filtration may lead to higher rates of blood cell hemolysis, which may contribute to attenuated cellular material crossing the membrane into the filtrate line, contaminating the filtrate (e.g., plasma) and decreasing integrity of the retentate (e.g., cellular material). Although both excessive fouling and high rates of hemolysis may be indicative of overaggressive filtration, each may not necessarily be indicative of the other. For example, a high rate of hemolysis may occur while the degree of fouling is normal, and a high degree of fouling may occur while the rate of hemolysis is normal.

Figure 1:
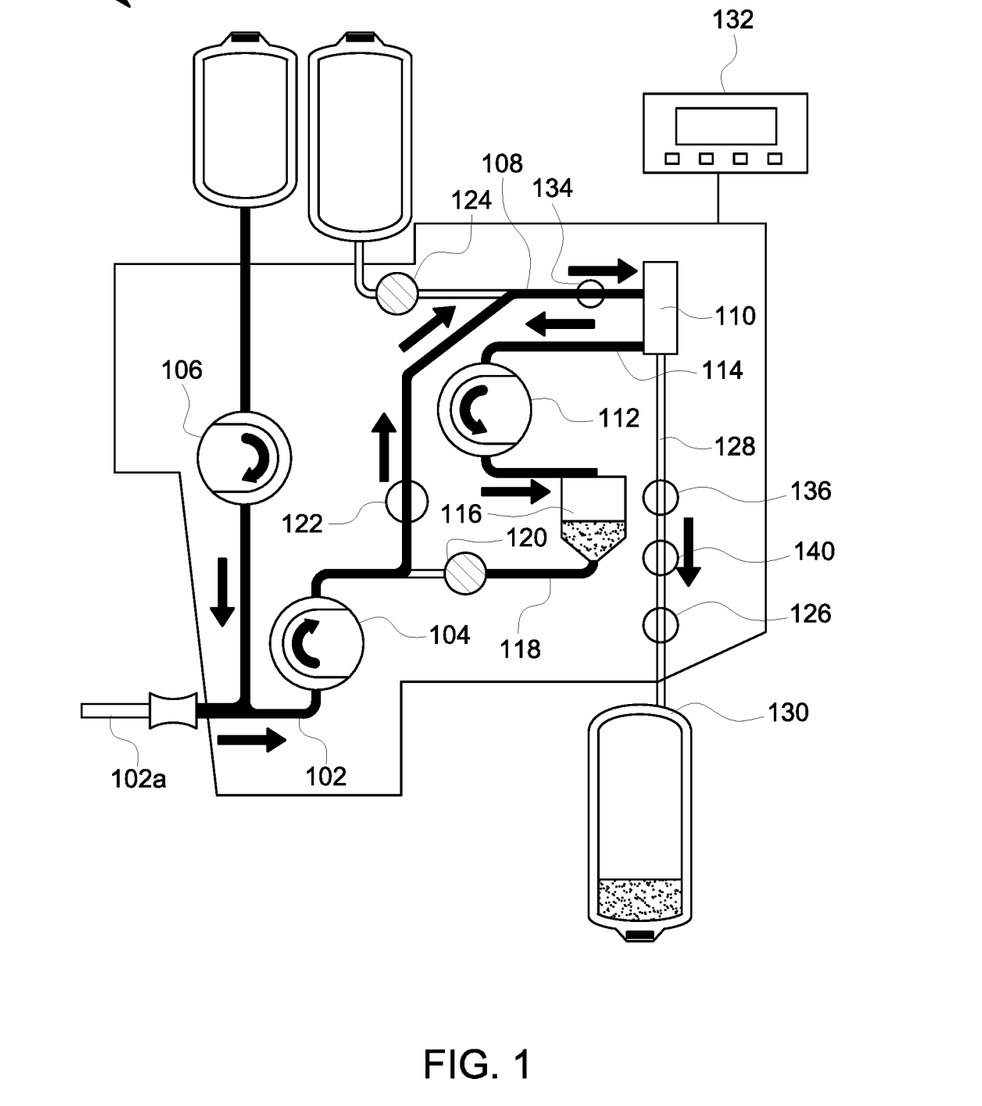
FIG. 1 is a schematic representation of a membrane filtration system, according to an exemplary embodiment.

FIG. 1 depicts a spinning membrane separation system 100 in the draw cycle of a biological fluid processing procedure. In one embodiment, blood components may be separated into plasma and its cellular components. It should be understood that the biological fluid procedure is described for illustrative purposes only, and the methods described herein may have applicability in a wide range of apheresis, concentration, washing, mixing, and medical fluid procedures.

The system 100 may include a source line 102 that may be configured to connect via an access device 102a to a fluid source, which may be a patient/donor or a source fluid container (not illustrated). Source line 102 may be acted on by a blood pump 104. In an embodiment in which source fluid is whole blood, anticoagulant may be added to the whole blood in the source line 102 by way of a second pump 106. The source line 102 may connect to a processing line 108 for introducing, e.g., anticoagulated whole blood, into the inlet of a spinning membrane separator 110. A third pump 112 may act on a first outlet line 114 to flow separated retentate (e.g., cellular material in a blood component procedure) to a container 116. In one embodiment, the contents of container 116 may be stored and/or further processed. In another embodiment, container 116 may be connected by way of return line 118 to the source line 102 for the return of the separated cellular material to, e.g., the donor. A filtrate line 128 may be connected to a second outlet of the separator 110 for flowing separated filtrate (e.g., plasma in a blood component procedure) to a filtrate collection container 130 for storage and/or further processing. Although not depicted in FIG. 1, in one embodiment, the filtrate container 130 may be connected to the source line 102 if an objective of the procedure is to, e.g., return the filtrate to the donor and instead collect the retentate.

Flow through the several lines may be selectively controlled by operation of clamps 120, 122, 124 and 126. The operation of the pumps 104, 106, 112, the clamps 120, 122, 124, 126, and the speed of rotation of the spinning membrane may be automatically controlled by a programmable controller 132. The controller 132 may be preprogrammed to operate the system 100 in accordance with a number of different separation protocols and may include a user interface to permit an operator to input information into and/or receive information from the controller. According to various embodiments, controller 132 may be integral to system 100 or remotely located with respect to system 100 (e.g., connected via cable and/or network).

Figure 2:
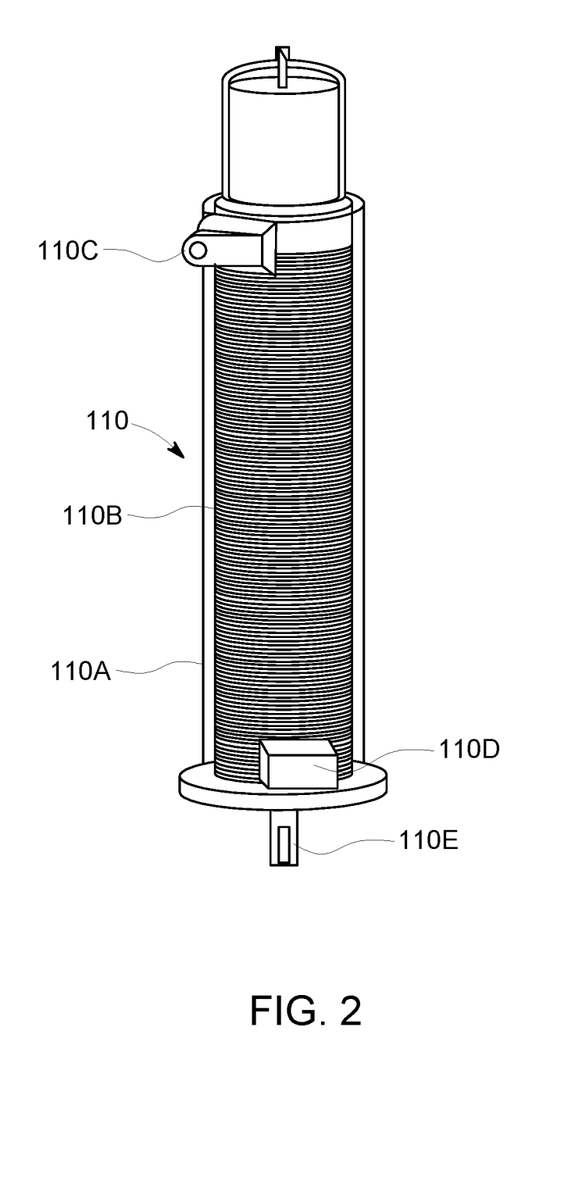
FIG. 2 is a schematic representation of a spinning membrane separator suitable for use in the system of FIG. 1, with portions shown in ghost line to show interior detail, according to an exemplary embodiment.

With reference to FIG. 2, the spinning membrane separator 110 may comprise a housing 110a, with a rotary spinner 110b mounted for relative rotation within the housing 110a and have a filter membrane on the surface thereof. The housing 110a may further include an inlet 110c in fluid communication with the processing line 108 of FIG. 1, a first outlet 110d in fluid communication with the retentate line 114, and a second outlet 110e in fluid communication with the filtrate line 128. Pressure sensors 134, 136 may be associated with the processing line 108, adjacent the inlet 110c, and the filtrate line 128, adjacent the second outlet 110e, respectively, for providing signals to the controller 132 by which the transmembrane pressure may be determined. An optical sensor 140 may be positioned along one or more lines 102, 108, 114, 128 and also provide signals to the controller 132 by which fluid properties within the lines may be determined. For example, in an embodiment in which blood components are being separated into cellular components and plasma, an optical sensor 140 may be placed along the filtrate line 128 for detecting free hemoglobin. Changes in free hemoglobin levels in the filtrate leading to changes in light transmission at certain wavelengths through the filtrate may be detected by the optical sensor 40 and used as a measure of occurrence and degree of hemolysis of blood cells. An example of an optical sensor is described in U.S. Pat. No. 6,419,822, which is incorporated by reference in its entirety, although the optical sensor may be of any suitable design or construction.

In response to a determination by the controller based on optical sensor inputs that the degree of hemolysis is higher than an authorized level, the controller may be configured to provide a response action that lowers the degree of hemolysis, suspends the procedure, and/or alerts an operator. Lowering the targeted hematocrit (HCT) of the retentate exiting the separator 110 has been shown to reduce hemolysis levels by lowering the aggressiveness/efficiency of filtration and thereby increase the amount of unfiltered plasma remaining in the retentate after exiting the separator 110. In an embodiment in which the outlet pump 112 is disposed along the retentate line 114, as depicted in FIG. 1, lowering the targeted HCT may be achieved by increasing the pump rate at pump 112. Increasing the pump rate at pump 112 may lower HCT of retentate by reducing the amount of flow through the membrane into the filtrate line 128 and thereby increase the volume of supernatant component in the retentate after exiting the separator 110. In an embodiment in which the outlet pump is disposed along the filtrate line 128 (embodiment not illustrated), lowering the targeted HCT may be achieved by decreasing the outlet pump rate.

During the biological fluid procedure, the controller may be programmed to process input from the optical sensor 140 to determine hemolysis levels to control the separation process. The optical sensor 140 may be used to control the separation process in lieu of or in addition to the previously mentioned separation control process based on membrane fouling measurements made by pressure sensors 134 and 136. In one embodiment, the controller may be programmed to control the separation process primarily based on membrane fouling measurements and secondarily on hemolysis measurements. For example, the controller may be programmed to lower targeted retentate HCT, e.g., by increasing retentate pump rate, based on hemolysis measurements only when membrane fouling is not detected, and programmed not to change targeted retentate HCT based on hemolysis measurements when membrane fouling has already initiated a protocol towards a response action. In another embodiment, the controller may be programmed to control the separation process equally based on membrane fouling measurements and hemolysis measurements. For example, the controller may be programmed to lower targeted retentate HCT based on hemolysis measurements only when membrane fouling is not detected, and also be programmed to initiate a protocol towards a response action based on membrane fouling measurements only when hemolysis is not detected.

Absolute free hemoglobin concentrations in blood may vary depending on a number of factors, including age of the blood after leaving a donor, donor characteristics, supernatant osmolality, etc. Therefore, the control process or algorithm for controlling separation based on hemolysis measurements may take into account free hemoglobin changes over time rather than absolute free hemoglobin measurements.

Control Process #1—Comparison of Current Hemoglobin to Past Hemoglobin

Figure 3:
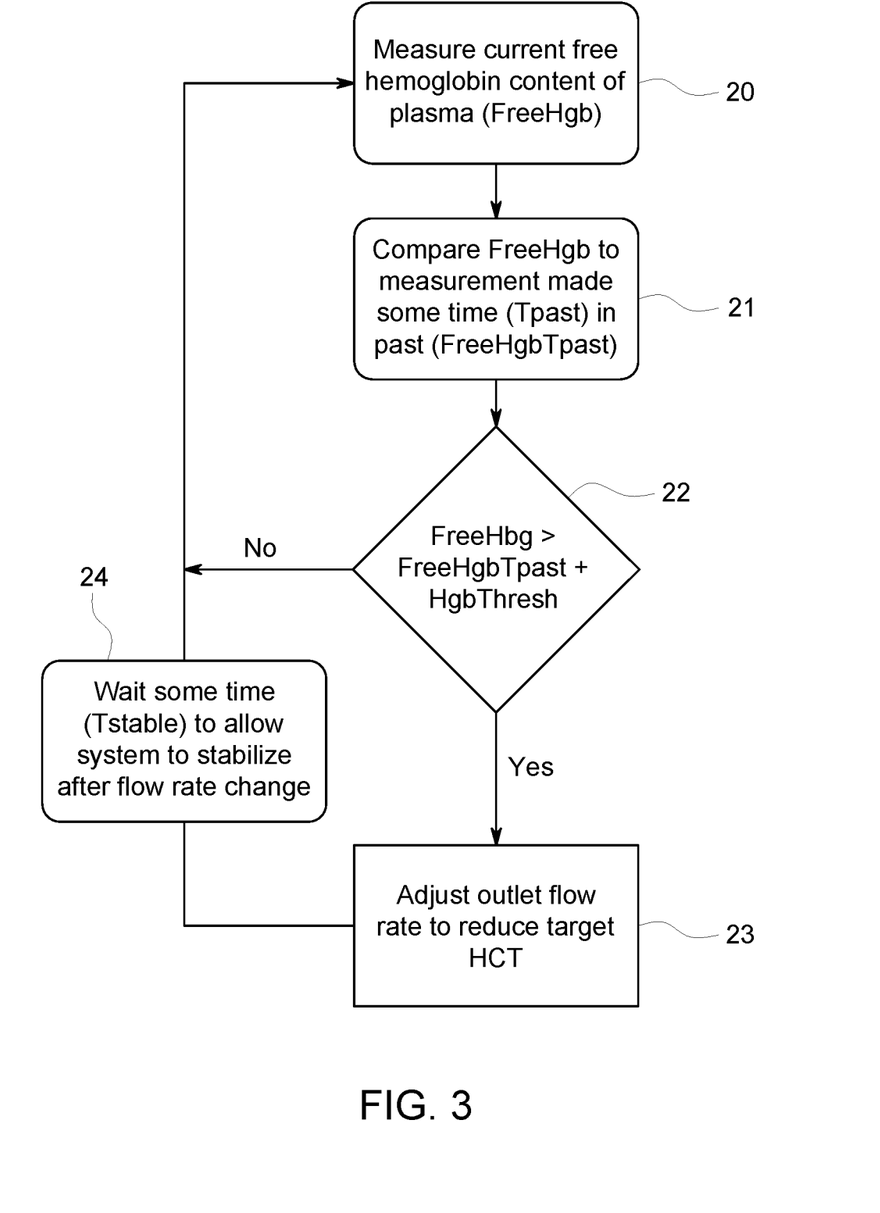
FIG. 3 is a flow diagram Illustrating measurement of hemoglobin and control of flow rate, according to an exemplary embodiment.

One embodiment of a control process or algorithm based on free hemoglobin changes over time may compare current hemoglobin measurements to a past hemoglobin measurement to monitor hemoglobin changes, e.g., increases, over a specific period of time. FIG. 3 shows a flow diagram of a control process or algorithm based on free hemoglobin continuously or periodically measured by the optical sensor 140 along the filtrate line 128 (FIG. 1). At step 20, a free hemoglobin measurement may be made and designated FreeHgb. At step 21, FreeHgb may be compared with a previous free hemoglobin measurement (FreeHgbTpast) made at a designated period of time (Tpast) prior to FreeHgb. At step 22, FreeHgb may be compared with the sum of FreeHgbTpast and a tolerance threshold (HgbThresh). If FreeHgb is not more than the sum of FreeHgbTpast and HgbThresh, the controller may be configured to withhold any response action and return to step 20 and repeat. If FreeHgb is greater than or equal to the sum of FreeHgbTpast and HgbThresh, the controller may be configured to lower the targeted retentate HCT to reduce hemolysis, e.g., by increasing retentate outlet flow rate, as shown in step 23. In one embodiment, the targeted retentate HCT may be lowered by 0.1-5%. In another embodiment, the targeted retentate HCT may be lowered by 1-2%. At step 24, the controller may be configured to wait a designated period of time (Tstable) to allow free hemoglobin measurements to stabilize in response to change of targeted retentate HCT prior to returning to step 20 for the next loop. Steps 20 to 24 may be repeated in a rolling fashion at a selected loop speed, e.g., 0.1 seconds.

Tpast and HgbThresh may be designated and programmed according to the level of sensitivity desired in the control process or algorithm. As HgbThresh decreases, the control process may become more sensitive to changes and may react to relatively small hemoglobin changes in the filtrate line. For a given HgbThresh value, as Tpast increases, the control process may become more sensitive to changes in hemoglobin levels because free hemoglobin levels are observed to generally increase as a fluid procedure runs its course. HgbThresh and Tpast may be selected or determined empirically based on factors such as sensitivity or noise of the optical sensor, level of hemolysis tolerance for a specific filtrate product, percentage by which targeted retentate HCT is lowered in the event of a response action, and/or hemolysis patterns of different fluid types. For example, a higher Tpast and higher HgbThresh may be desirable if the optical sensor is shown to detect oscillating or noisy hemoglobin signals so that the oscillation or noise may be less represented in the sum of FreeHgbPast and HgbThresh. In another example, a lower HgbThresh may be desirable if the level of hemolysis tolerance for a specific filtrate product is low. Based on different fluid procedure systems, sensitivities, and settings, the configurable parameters HgbThresh, TPast, and Tstable may be empirically determined.

Example 1

| | |
|---|---|
| HgbThresh: 10 mg/dL | 12 mg/dL < 5 mg/dL + 10 mg/dL |
| TPast: 10 sec | (No change in targeted outlet HCT) |
| FreeHgb: 12 mg/dL | |
| FreeHgbPast: 5 mg/dL | |

Example 1 above describes a scenario in which the sum of FreeHgbPast and HgbThresh is larger than FreeHgb. The control process or algorithm at step 22 of FIG. 3 shows that in this example, the controller is configured to produce no change in the targeted outlet HCT.

Example 2

| | |
|---|---|
| HgbThresh: 5 mg/dL | 12 mg/dL > 5 mg/dL + 5 mg/dL |
| TPast: 10 sec | (Response action) |
| FreeHgb: 12 mg/dL | |
| FreeHgbPast: 5 mg/dL | |

Example 2 above describes a scenario in which the sum of FreeHgbPast and HgbThresh is less than FreeHgb. The control process or algorithm at step 22 of FIG. 3 shows that in this example, the controller is configured to move on to step 23 and produce a response action, such as lowering the targeted retentate HCT, e.g., by 0.1-5%. At step 24, the controller may be configured to wait a designated period of time (Tstable) to allow free hemoglobin measurements to stabilize in response to change of targeted retentate HCT prior to returning to step 20 for the next loop.

Example 3

| | |
|---|---|
| HgbThresh: 10 mg/dL | 12 mg/dL > 1 mg/dL + 10 mg/dL |
| TPast: 15 sec | (Response action) |
| FreeHgb: 12 mg/dL | |
| FreeHgbPast: 1 mg/dL | |

Example 3 above describes a scenario in which the sum of FreeHgbPast and HgbThresh is less than FreeHgb in response to raising TPast to 15 seconds in comparison to TPast (10 seconds) in Example 1. Elevating TPast has had the effect of increasing the discrepancy between FreeHgbPast and FreeHbg, triggering the control process or algorithm at step 22 to move on to step 23 and produce a response action, in contrast to Example 1. At step 24, the controller may be configured to wait a designated period of time (Tstable) to allow free hemoglobin measurements to stabilize in response to change of targeted retentate HCT prior to returning to step 20 for the next loop.

Control Process #2—Comparison of Current Δhemoglobin to Threshold Δhemoglobin

Figure 4:
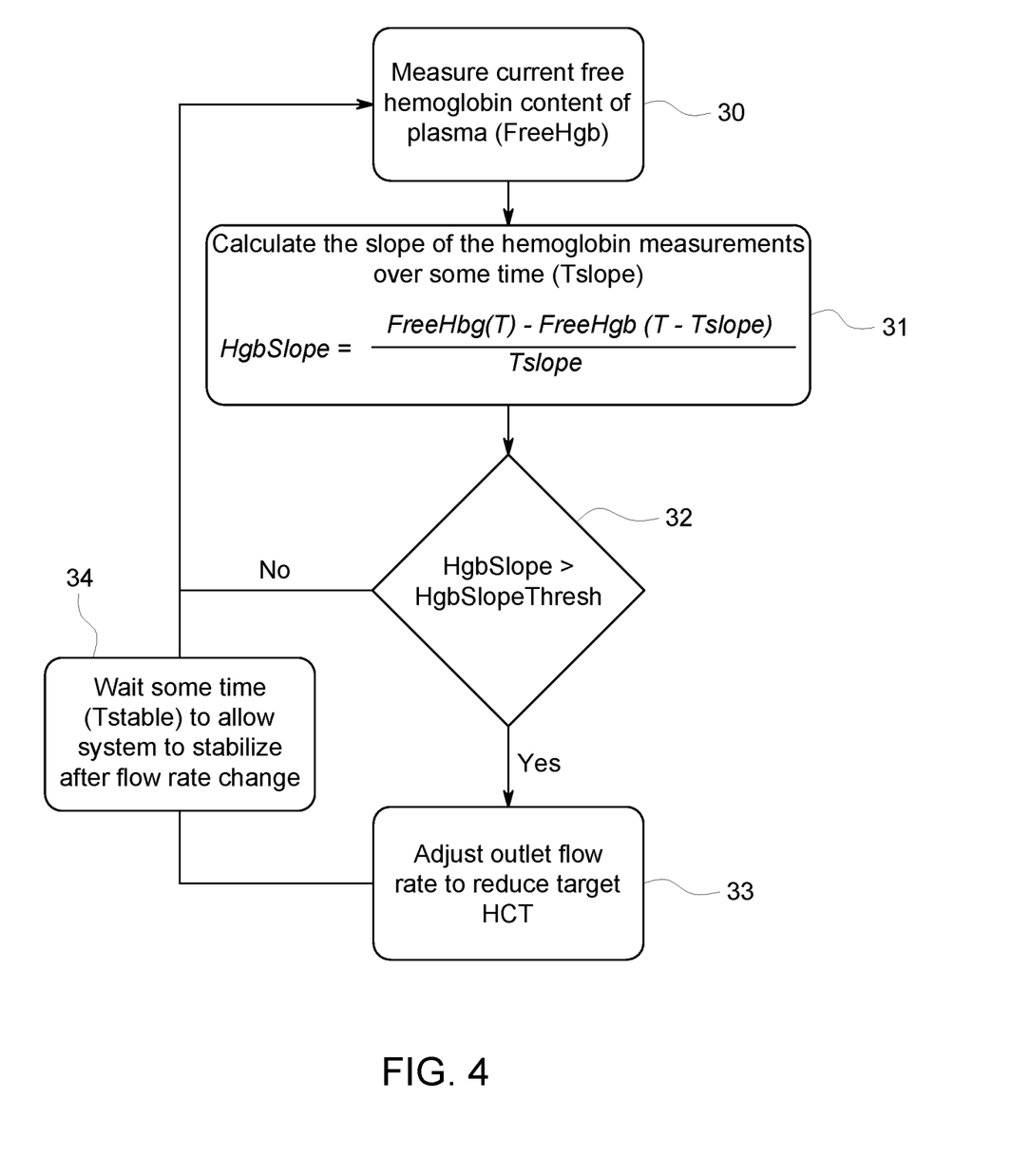
FIG. 4 is a flow diagram illustrating measurement of hemoglobin and control of flow rate, according to another exemplary embodiment.

Another embodiment of a control process or algorithm based on free
hemoglobin changes over time may compare current hemoglobin rate of change $$\left(\frac{\Delta Hgb}{\Delta t}\right)$$

to an empirically derived rate of change threshold to monitor hemoglobin changes, e.g., increases, over a specific period of time. FIG. 4 shows a flow diagram of a control process or algorithm based on free hemoglobin continuously measured by the optical sensor 140 along the filtrate line 128 (FIG. 1). At step 30, a free hemoglobin measurement may be made and designated FreeHgb(T). At step 31, a free hemoglobin rate of change over a period of time (Tslope) may be calculated and designated HgbSlope. HgbSlope may be calculated by subtracting hemoglobin levels at a past time (FreeHgb(T-TSlope)) from hemoglobin levels at a current time (FreeHgb(T)) and dividing the difference by the period of time Tslope. At step 32, HgbSlope may be compared with an empirically derived slope threshold (HgbSlopeThresh). If HgbSlope is not more than HgbSlopeThresh, the controller may be configured to withhold any response action and return to step 30 and repeat. If HgbSlope is greater than or equal to HgbSlopeThresh, the controller may be configured to lower the targeted retentate HCT to reduce hemolysis, e.g., by increasing retentate outlet flow rate, as shown in step 33. In one embodiment, the targeted retentate HCT may be lowered by 0.1-5%. At step 34, the controller may be configured to wait a designated period of time (Tstable) to allow free hemoglobin measurements to stabilize in response to change of targeted retentate HCT prior to returning to step 30 for the next loop.

Tslope, HgbSlopeThresh, and Tstable may be designated and programmed according to the level of sensitivity desired in the control process. As HgbSlopeThresh decreases, the control process or algorithm may become more sensitive to changes and may react to relatively small hemoglobin changes in the filtrate line. For a given HgbSlopeThresh value, as Tslope decreases, the control process may become more sensitive to changes in hemoglobin levels because changes in free hemoglobin levels are observed to generally decrease as a fluid procedure runs its course compared to the beginning of the fluid procedure. HgbSlopeThresh, Tslope, and Tstable may be selected or determined empirically based on factors such as sensitivity or noise of the optical sensor, level of hemolysis tolerance for a specific filtrate product, percentage by which targeted retentate HCT is lowered in the event of a response action, and/or hemolysis patterns of different fluid types. For example, a higher Tslope and higher HgbSlopeThresh may be desirable if the optical sensor is shown to detect oscillating or noisy hemoglobin signals so that the oscillation or noise may be less represented in the HgbSlope. In another example, a lower HgbSlopeThresh may be desirable if the level of hemolysis tolerance for a specific filtrate product is low. In another example, a lower Tstable may be desirable if hemolysis tolerance is low so that the reaction time may be shorter after each change is made. Based on different fluid procedure systems, sensitivities, and settings, the configurable parameters HgbSlopeThresh, Tslope, and Tstable may be empirically determined.

Example 4

HgbSlopeThresh: 0.9 mg/dL/sec
Tslope: 10 sec
FreeHgb(T): 12 mg/dL
FreeHgb(T-TSlope): 5 mg/dL $$\frac{12\frac{mg}{dL} - 5\frac{mg}{dL}}{10\ sec} < 0.9\ mg/dL/sec$$

(No change in targeted outlet HCT)

Example 4 above describes a scenario in which HgbSlopeThresh is larger than HgbSlope. The control process or algorithm at step 32 of FIG. 4 shows that in this example, the controller is configured to produce no change in the targeted outlet HCT.

Example 5

HgbSlopeThresh: 0.5 mg/dL/sec
Tslope: 10 sec
FreeHgb(T): 12 mg/dL
FreeHgb(T-TSlope): 5 mg/dL $$\frac{12\frac{mg}{dL} - 5\frac{mg}{dL}}{10\ sec} > 0.5\ mg/dL/sec$$

(Response action)

Example 5 above describes a scenario in which HgbSlopeThresh is less than HgbSlope. The control process or algorithm at step 32 of FIG. 4 shows that in this example, the controller is configured to move on to step 33 and produce a response action, such as lowering the targeted retentate HCT, e.g., by 0.1-5%. At step 34, the controller may be configured to wait a designated period of time (Tstable) to allow free hemoglobin measurements to stabilize in response to change of targeted retentate HCT prior to returning to step 30 for the next loop.

Example 6

HgbSlopeThresh: 0.9 mg/dL/sec
Tslope: 2 sec
FreeHgb(T): 12 mg/dL
FreeHgb(T-TSlope): 10 mg/dL $$\frac{12\frac{mg}{dL} - 10\frac{mg}{dL}}{2\ sec} > 0.9\ mg/dL/sec$$

(Response action)

Example 6 above describes a scenario in which HgbSlopeThresh is less than HgbSlope in response to decreasing TSlope to 2 seconds in comparison to TSlope (10 seconds) in Example 1. Lowering TSlope has had the effect of increasing HgbSlope, triggering the control process or algorithm at step 32 to move on to step 33 and produce a response action, in contrast to Example 1. At step 34, the controller may be configured to wait a designated period of time (Tstable) to allow free hemoglobin measurements to stabilize in response to change of targeted retentate HCT prior to returning to step 30 for the next loop.

Figure 5:
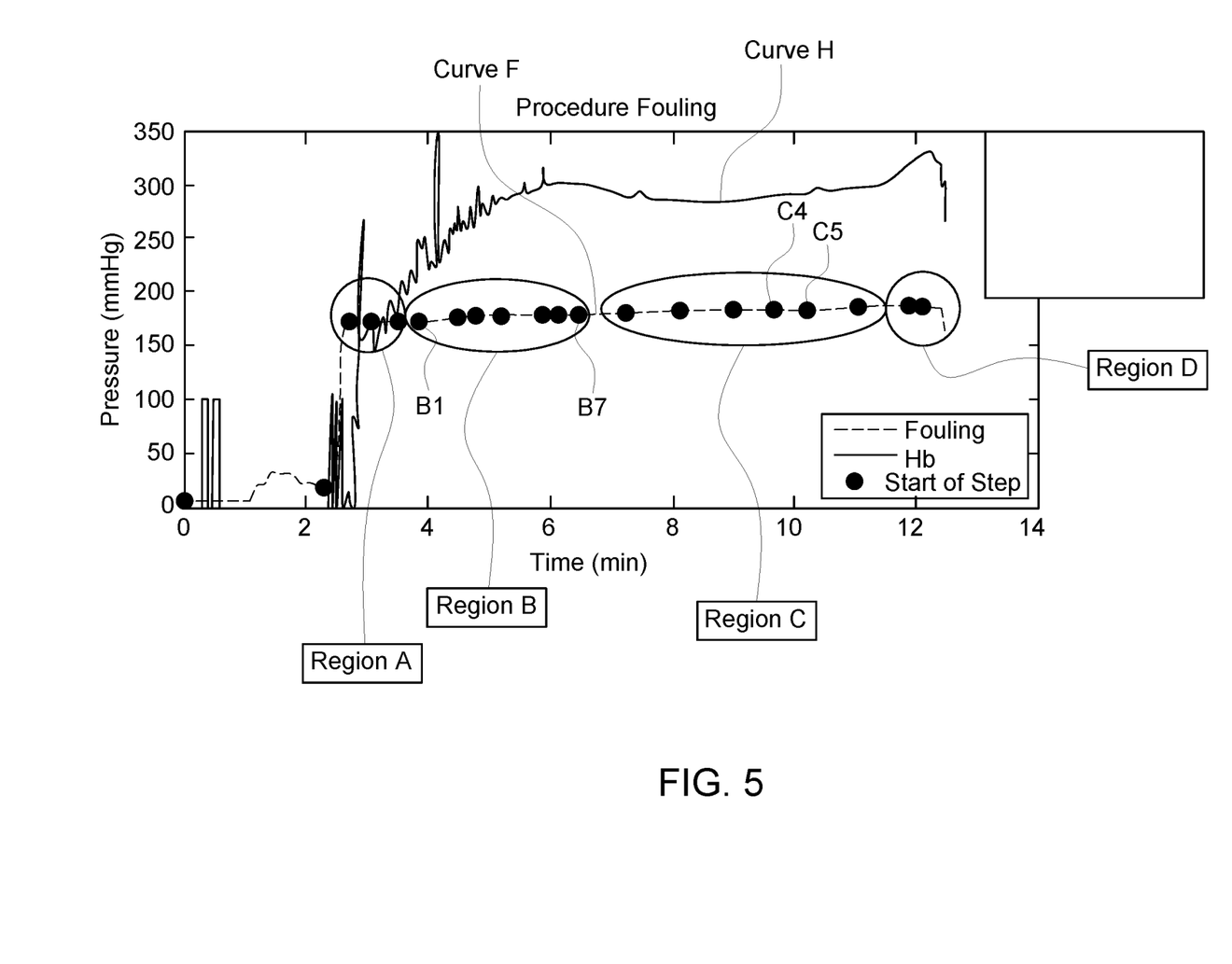
FIG. 5 is a graphical representation of a separation control process over a period of time based on free hemoglobin measurements and membrane fouling measurements, according to an exemplary embodiment.

FIG. 5 is a graphical representation of a separation control process being made over time based on free hemoglobin changes as well as membrane fouling measurements. Curve F represents TMP of the separator over time and is a result of the controller monitoring and adjusting the targeted retentate HCT based on a fouling rate control process or algorithm, such as those described in the aforementioned U.S. Pat. No. 8,840,790 and U.S. Provisional Pat. Appl. No. 62/334,249. Curve H represents hemoglobin content of the filtrate line over time and is a result of the controller monitoring and adjusting the targeted retentate HCT based on a hemoglobin control process such as control processes #1 and #2. Curve H is drawn with arbitrary units representative of hemoglobin levels registered by the controller. For example, curve H may reflect light transmission values at a certain wavelength, e.g., green light, measured by the optical sensor that are converted to hemoglobin levels before initiating the hemoglobin control process or algorithm. The circular data points overlaid over curve F represent times at which the targeted HCT was changed based on the fouling rate control process and/or the hemoglobin control process.

Region A of FIG. 5 comprises three time points (circular dots) at which the targeted HCT values were changed based on the fouling rate control process, which may be configured to increase targeted HCT when no fouling is detected as defined by the fouling rate control process. Region A shows that the targeted HCT was increased three consecutive times without triggering the hemoglobin control process.

Region B comprises seven time points at which the targeted HCT values were changed based on the fouling rate control process as well as the hemoglobin control process. Point B1 represents the start of region B at which the fouling control process did not detect fouling and would have continued to increase targeted HCT but for the rising hemolysis levels triggering the hemoglobin control process, which took precedence over the fouling control process and decreased the targeted HCT. Point B7 represents the last instance in region B the hemoglobin control process overrode the fouling control process to decrease the rate at which hemolysis is generated.

Region C comprises six time points at which the targeted HCT values were increased based on the fouling control process without interference from the hemoglobin control process, due to hemoglobin levels being fairly stable and fouling rates remaining acceptable throughout region C. Region D comprises two time points before the end of the fluid procedure at which the targeted HCT values were lowered after the optical sensor's detection of rising hemolysis levels and triggering of the hemoglobin control process, which decreased the targeted HCT twice prior to the end of the procedure.

Without limiting the foregoing description, in accordance with one aspect of the subject matter herein, there is provided a computer-implemented method for controlling fluid flow rates during a biological fluid procedure, comprising providing a membrane separator configured to separate a biological fluid into filtrate and retentate. Concentration of retentate exiting the membrane separator is controllable by altering a flow rate of the retentate exiting the membrane separator. The computer-implemented method also comprises detecting a change of attenuated retentate particles within the filtrate, comparing the change of attenuated retentate particles within the filtrate with a threshold level, and providing a response action comprising altering the concentration of retentate exiting the membrane separator if the change of attenuated retentate particles within the filtrate exceeds the threshold level.

In accordance with a second aspect which may be used or combined with the immediately preceding aspect, the biological fluid comprises blood, the filtrate comprises plasma, the retentate comprises cellular components, and the attenuated retentate particles comprise free hemoglobin.

In accordance with a third aspect which may be used or combined with any of the preceding aspects, the change of attenuated retentate particles within the filtrate is detected with an optical sensor.

In accordance with a fourth aspect which may be used or combined with any of the preceding aspects, the method further comprises detecting a change in transmembrane pressure within the membrane separator, comparing the change in transmembrane pressure with a second threshold level, and providing a second response action comprising increasing the flow rate of the retentate if the change in transmembrane pressure exceeds the second threshold level. The second response action is provided only when the first response action is not triggered.

In accordance with a fifth aspect which may be used or combined with any of the preceding aspects, the method comprises detecting a change in transmembrane pressure within the membrane separator, comparing the change in transmembrane pressure with a second threshold level, providing a second response action comprising increasing the flow rate of the retentate if the change in transmembrane pressure exceeds the second threshold level, and withholding the first response action when the second response action is ongoing.

In accordance with a sixth aspect which may be used or combined with any of the preceding aspects, the concentration of retentate exiting the membrane separator is altered by altering a pump rate of a pump disposed along a retentate fluid pathway.

In accordance with a seventh aspect which may be used or combined with any of the preceding aspects, the concentration of retentate exiting the membrane separator is altered by altering a pump rate of a pump disposed along a filtrate fluid pathway.

In accordance with an eighth aspect which may be used or combined with any of the preceding aspects, detecting the change of attenuated retentate particles within the filtrate comprises detecting a first level of attenuated retentate particles at a first point in time and detecting a second level of attenuated retentate particles at a designated time after the first point in time. Comparing the change of attenuated retentate particles within the filtrate with the threshold level comprises comparing a sum of the first level of attenuated retentate particles and the threshold level with the second level of attenuated retentate particles.

In accordance with a ninth aspect which may be used or combined with the immediately preceding aspect, the designated time after the first point in time and the threshold level are empirically determined.

In accordance with a tenth aspect which may be used or combined with any of the preceding aspects, detecting the change of attenuated retentate particles within the filtrate comprises detecting a first level of attenuated retentate particles at a first point in time and detecting a second level of attenuated retentate particles at a designated time after the first point in time. Comparing the change of attenuated retentate particles within the filtrate with the threshold level comprises comparing a rate of change over the designated time between the first level and second level with the threshold level.

In accordance with an eleventh aspect which may be used or combined with any of the preceding aspects, if a response action is provided, the method further comprises waiting a designated period time after providing the response action before providing a next response action.

In accordance with a twelfth aspect which may be used or combined with any of the preceding aspects, the response action comprises altering the concentration of the retentate exiting the membrane separator by 0.1-5%.

In accordance with a thirteenth aspect, there is provided a system for automated control and processing of a biological fluid flow, the system comprising a reusable separation apparatus controlled by a microprocessing controller unit. The system also comprises a disposable sterile circuit configured to associate with the reusable separation apparatus, the disposable sterile circuit comprising a membrane separator comprising a porous membrane, wherein the separator comprises an inlet, a first outlet for retentate, and a second outlet for filtrate. The reusable apparatus and microprocessing controller unit are configurable with an output concentration of retentate and configured to detect at the second outlet a change of attenuated retentate particles within the filtrate, compare the change of attenuated retentate particles with a threshold level, and provide a response action comprising altering the output concentration of retentate exiting the first outlet if the change of attenuated retentate particles exceeds the threshold level.

In accordance with a fourteenth aspect which may be used or combined with the immediately preceding aspect, the reusable apparatus and microprocessing controller unit are further configured to detect an change in transmembrane pressure within the membrane separator, compare the change in transmembrane pressure with a second threshold level, provide a second response action comprising lowering a flow rate at the first outlet if the change in transmembrane pressure exceeds the second threshold level, and withhold the first response action while the second response action is ongoing.

In accordance with a fifteenth aspect which may be used or combined with the thirteenth aspect, the concentration of retentate exiting the membrane separator is altered by altering a pump rate of a pump associated with the first outlet or the second outlet.

In accordance with a sixteenth aspect which may be used or combined with the thirteenth aspect, detecting the change of attenuated retentate particles comprises detecting a first level of attenuated retentate particles at a first point in time and detecting a second level of attenuated retentate particles at a designated time after the first point in time. Comparing the change of attenuated retentate particles with the threshold level comprises comparing a sum of the first level of attenuated retentate particles and the threshold level with the second level of attenuated retentate particles.

In accordance with a seventeenth aspect which may be used or combined with any of the immediately preceding aspect, the designated time after the first point in time and the threshold level are empirically determined.

In accordance with an eighteenth aspect which may be used or combined with the thirteenth aspect, detecting the change of attenuated retentate particles comprises detecting a first level of attenuated retentate particles at a first point in time and detecting a second level of attenuated retentate particles at a designated time after the first point in time. Comparing the change of attenuated retentate particles with the threshold level comprises comparing a rate of change over the designated time between the first level and second level with the threshold level.

In accordance with a nineteenth aspect which may be used or combined with the thirteenth aspect, if a response action is provided by the reusable apparatus and microprocessing controller unit, the reusable apparatus and microprocessing controller unit are configured to wait a designated period of time after providing the response action before providing a next response action.

In accordance with a twentieth aspect, there is provided a computer-implemented method for controlling fluid flow rates during a blood processing procedure, comprising providing a spinning membrane separator configured to separate blood into plasma and cellular components, wherein hematocrit of the cellular components exiting the spinning membrane separator is controllable by altering a flow rate of the cellular components exiting the membrane separator. The computer-implemented method also comprises detecting a change of free hemoglobin within the plasma with an optical sensor, detecting a change in transmembrane pressure within the spinning membrane separator with a pressure sensor, comparing the change of free hemoglobin within the plasma with a first threshold level, comparing the change in transmembrane pressure with a second threshold level, altering the flow rate of the cellular components exiting the spinning membrane separator if the change of free hemoglobin exceeds the first threshold level, and altering the flow rate of the cellular components exiting the spinning membrane separator if the change of transmembrane pressure exceeds the second threshold level. The flow rate is not altered based on the change of free hemoglobin if the flow rate is already being altered based on the change of transmembrane pressure, and the flow rate is not altered based on the change of transmembrane pressure if the flow rate is already being altered based on the change of free hemoglobin.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A computer-implemented method for controlling fluid flow rates during a biological fluid procedure, comprising:
    providing a membrane separator configured to separate a biological fluid into filtrate and retentate, wherein concentration of retentate exiting the membrane separator is controllable by altering a flow rate of the retentate exiting the membrane separator;
    detecting a change of attenuated retentate particles within the filtrate;
    comparing the change of attenuated retentate particles within the filtrate with a threshold level; and
    providing a first response action comprising altering the concentration of retentate exiting the membrane separator if the change of attenuated retentate particles within the filtrate exceeds the threshold level;
    detecting a change in transmembrane pressure within the membrane separator;
    comparing the change in transmembrane pressure with a second threshold level; and providing a second response action comprising increasing the flow rate of the retentate if the change in transmembrane pressure exceeds the second threshold level,
    wherein the second response action is provided only when the first response action is not triggered; or
    withholding the first response action when the second response action is ongoing.

2. The computer-implemented method of claim 1, wherein the biological fluid comprises blood, the filtrate comprises plasma, the retentate comprises cellular components, and the attenuated retentate particles comprise free hemoglobin.

3. The computer-implemented method of claim 1, further comprising detecting the change of attenuated retentate particles within the filtrate with an optical sensor.

4. The computer-implemented method of claim 1, further comprising altering the concentration of retentate exiting the membrane separator by altering a pump rate of a pump disposed along a retentate fluid pathway.

5. The computer-implemented method of claim 1, further comprising altering the concentration of retentate exiting the membrane separator by altering a pump rate of a pump disposed along a filtrate fluid pathway.

6. The computer-implemented method of claim 1, wherein:
    detecting the change of attenuated retentate particles within the filtrate comprises detecting a first level of attenuated retentate particles at a first point in time and detecting a second level of attenuated retentate particles at a designated time after the first point in time; and
    comparing the change of attenuated retentate particles within the filtrate with the threshold level comprises comparing a sum of the first level of attenuated retentate particles and the threshold level with the second level of attenuated retentate particles.

7. The computer-implemented method of claim 6, wherein the designated time after the first point in time and the threshold level are empirically determined.

8. The computer-implemented method of claim 1, wherein:
    detecting the change of attenuated retentate particles within the filtrate comprises detecting a first level of attenuated retentate particles at a first point in time and detecting a second level of attenuated retentate particles at a designated time after the first point in time; and
    comparing the change of attenuated retentate particles within the filtrate with the threshold level comprises comparing a rate of change over the designated time between the first level and second level with the threshold level.

9. The computer-implemented method of claim 1, wherein if a response action is provided, the method further comprises waiting a designated period time after providing the response action before providing a next response action.

10. The computer-implemented method of claim 1, wherein the response action comprises altering the concentration of the retentate exiting the membrane separator by 0.1-5%.

11. A system for automated control and processing of a biological fluid flow, the system comprising:
    a reusable separation apparatus controlled by a microprocessing controller unit;

a disposable sterile circuit configured to associate with the reusable separation apparatus, the disposable sterile circuit comprising a membrane separator comprising a porous membrane, wherein the separator comprises an inlet, a first outlet for retentate, and a second outlet for filtrate;

wherein the reusable apparatus and microprocessing controller unit are configurable with an output concentration of retentate and configured to:
1) detect at the second outlet a change of attenuated retentate particles within the filtrate;
2) compare the change of attenuated retentate particles with a threshold level; and
3) provide a response action comprising altering the output concentration of retentate exiting the first outlet if the change of attenuated retentate particles exceeds the threshold level;
4) detect a change in transmembrane pressure within the membrane separator;
5) compare the change in transmembrane pressure with a second threshold level;
6) provide a second response action comprising increasing the flow rate of the retentate if the change in transmembrane pressure exceeds the second threshold level; and
7) provide the second response action only when the first response action is not triggered; or withhold the first response action while the second response action is ongoing.

12. The system of claim 11, further comprising altering the concentration of retentate exiting the membrane separator by altering a pump rate of a pump associated with the first outlet or the second outlet.

13. The system of claim 11, wherein:
detecting the change of attenuated retentate particles comprises detecting a first level of attenuated retentate particles at a first point in time and detecting a second level of attenuated retentate particles at a designated time after the first point in time; and
comparing the change of attenuated retentate particles with the threshold level comprises comparing a sum of the first level of attenuated retentate particles and the threshold level with the second level of attenuated retentate particles.

14. The system of claim 13, wherein the designated time after the first point in time and the threshold level are empirically determined.

15. The system of claim 11, wherein:
detecting the change of attenuated retentate particles comprises detecting a first level of attenuated retentate particles at a first point in time and detecting a second level of attenuated retentate particles at a designated time after the first point in time; and
comparing the change of attenuated retentate particles with the threshold level comprises comparing a rate of change over the designated time between the first level and second level with the threshold level.

16. The system of claim 11, wherein if a response action is provided by the reusable apparatus and microprocessing controller unit, the reusable apparatus and microprocessing controller unit are configured to wait a designated period of time after providing the response action before providing a next response action.

17. A computer-implemented method for controlling fluid flow rates during a blood processing procedure, comprising:
providing a spinning membrane separator configured to separate blood into plasma and cellular components, wherein hematocrit of the cellular components exiting the spinning membrane separator is controllable by altering a flow rate of the cellular components exiting the membrane separator;
detecting a change of free hemoglobin within the plasma with an optical sensor;
detecting a change in transmembrane pressure within the spinning membrane separator with a pressure sensor;
comparing the change of free hemoglobin within the plasma with a first threshold level;
comparing the change in transmembrane pressure with a second threshold level;
altering the flow rate of the cellular components exiting the spinning membrane separator if the change of free hemoglobin exceeds the first threshold level; altering the flow rate of the cellular components exiting the spinning membrane separator if the change of transmembrane pressure exceeds the second threshold level;
wherein the flow rate is not altered based on the change of free hemoglobin if the flow rate is already being altered based on the change of transmembrane pressure, and the flow rate is not altered based on the change of transmembrane pressure if the flow rate is already being altered based on the change of free hemoglobin.

* * * * *